(12) United States Patent
Patrick et al.

(10) Patent No.: US 7,524,275 B2
(45) Date of Patent: Apr. 28, 2009

(54) DRUG ELUTING BRACHYTHERAPY METHODS AND APPARATUS

(75) Inventors: Timothy J. Patrick, Alpharetta, GA (US); James B. Stubbs, Alpharetta, GA (US)

(73) Assignee: Cytyc Corporation, Marlborough, MA (US)

( * ) Notice: Subject to any disclaimer, the term of this patent is extended or adjusted under 35 U.S.C. 154(b) by 640 days.

(21) Appl. No.: 10/714,586

(22) Filed: Nov. 14, 2003

(65) Prior Publication Data

US 2005/0107653 A1 May 19, 2005

(51) Int. Cl.
*A61N 5/00* (2006.01)
(52) U.S. Cl. .............................. 600/2; 600/3
(58) Field of Classification Search ................ 600/1–7; 604/19, 48, 57, 93.01, 96.01, 103.02, 264–266, 604/272, 290, 500, 506–511, 522; 606/191–200; 128/897–899
See application file for complete search history.

(56) References Cited

U.S. PATENT DOCUMENTS

| | | | | |
|---|---|---|---|---|
| 3,324,847 A | 6/1967 | Zoumboulis | ................ | 128/1.2 |
| 3,872,856 A | 3/1975 | Clayton | ................ | 128/1.2 |
| 4,417,576 A | 11/1983 | Baran | ................ | 128/207.15 |
| 4,706,652 A | 11/1987 | Horowitz | ................ | 128/1.2 |
| 4,754,745 A | 7/1988 | Horowitz | ................ | 128/1.2 |
| 4,763,642 A | 8/1988 | Horowitz | ................ | 128/1.2 |
| 4,821,725 A | 4/1989 | Azam et al. | ............. | 128/420 A |
| 4,867,741 A | 9/1989 | Portnoy | ................ | 604/10 |
| 5,030,195 A | 7/1991 | Nardi | ................ | 600/7 |
| 5,084,001 A | 1/1992 | Van't Hooft et al. | ........... | 600/3 |
| 5,084,015 A | 1/1992 | Moriuchi | ................ | 604/96 |
| 5,106,360 A | 4/1992 | Ishiwara et al. | ................ | 600/2 |
| 5,112,303 A | 5/1992 | Pudenz et al. | ................ | 604/49 |
| 5,152,747 A | 10/1992 | Olivier | ................ | 604/93 |
| 5,236,410 A | 8/1993 | Granov et al. | ................ | 600/12 |
| 5,286,254 A * | 2/1994 | Shapland et al. | ............. | 604/21 |
| 5,342,348 A * | 8/1994 | Kaplan | ................ | 604/891.1 |
| 5,422,926 A * | 6/1995 | Smith et al. | ................ | 378/121 |

(Continued)

FOREIGN PATENT DOCUMENTS

DE    198 19 426 A 1    11/1999

(Continued)

OTHER PUBLICATIONS

Ashpole, R.D. et al., "A New Technique of Brachytherapy for Malignant Gliomas with Caesium-137: A New Method Utilizing a Remote Afterloading System," Clinical Oncology, vol. 2, 333-7 (1990).

(Continued)

*Primary Examiner*—John P Lacyk
(74) *Attorney, Agent, or Firm*—Heather Larson (57) ABSTRACT

An interstitial brachytherapy apparatus and methods for treating proliferative tissue disorders with radiation and a surface delivered treatment agent. The brachytherapy device includes an insertion member having proximal and distal portions and at least one lumen extending therethrough. An expandable surface member is mated to the distal portion of the insertion member and includes a treatment agent releasably mated thereon. When the brachytherapy device is positioned within a tissue cavity and the expandable surface member is expanded, at least a portion of the treatment agent is delivered to tissue surrounding the tissue cavity.

28 Claims, 5 Drawing Sheets

U.S. PATENT DOCUMENTS

| | | | | |
|---|---|---|---|---|
| 5,429,582 | A | 7/1995 | Williams | 600/2 |
| 5,484,384 | A | 1/1996 | Fearnot | 600/3 |
| 5,503,613 | A | 4/1996 | Weinberger | 600/3 |
| 5,566,221 | A | 10/1996 | Smith et al. | 378/145 |
| 5,611,767 | A | 3/1997 | Williams | 600/2 |
| 5,662,580 | A | 9/1997 | Bradshaw et al. | 600/3 |
| 5,707,332 | A | 1/1998 | Weinberger | 600/3 |
| 5,713,828 | A | 2/1998 | Coniglione | 600/7 |
| 5,720,717 | A | 2/1998 | D'Andrea | 604/21 |
| 5,764,723 | A | 6/1998 | Weinberger et al. | 378/65 |
| 5,782,742 | A | 7/1998 | Crocker et al. | 600/3 |
| 5,785,688 | A | 7/1998 | Joshi et al. | 604/141 |
| 5,993,374 | A | 11/1999 | Kick | 600/8 |
| 6,001,054 | A | 12/1999 | Regulla et al. | |
| 6,036,631 | A | 3/2000 | McGrath et al. | 600/3 |
| 6,048,299 | A | 4/2000 | Hoffmann | 600/3 |
| 6,120,523 | A | 9/2000 | Crocker et al. | 606/192 |
| 6,149,574 | A | 11/2000 | Trauthen et al. | 600/3 |
| 6,176,821 | B1 | 1/2001 | Crocker et al. | 600/3 |
| 6,261,320 | B1 | 7/2001 | Tam et al. | 623/1.15 |
| 6,287,249 | B1 | 9/2001 | Tam et al. | 600/3 |
| 6,409,716 | B1 * | 6/2002 | Sahatjian et al. | 604/509 |
| 6,419,692 | B1 * | 7/2002 | Yang et al. | 623/1.15 |
| 6,458,069 | B1 * | 10/2002 | Tam et al. | 600/3 |
| 6,471,630 | B1 | 10/2002 | Sioshansi et al. | 600/1 |
| 6,487,438 | B1 | 11/2002 | Widmark et al. | 600/431 |
| 6,645,135 | B1 | 11/2003 | Bhat | |
| 6,918,869 | B2 * | 7/2005 | Shaw et al. | 600/3 |
| 2002/0055667 | A1* | 5/2002 | Mavity et al. | 600/3 |
| 2003/0028097 | A1 | 2/2003 | D'Amico et al. | 600/427 |
| 2003/0114878 | A1 | 6/2003 | Diederich et al. | 606/192 |

FOREIGN PATENT DOCUMENTS

| | | |
|---|---|---|
| EP | 0340881 | 11/1989 |
| EP | 0867200 | 9/1998 |
| EP | 0 970 724 A2 | 1/2000 |
| GB | 2105201 | 3/1983 |
| WO | 9210932 | 7/1992 |
| WO | 9309724 | 5/1993 |
| WO | 9719723 | 6/1997 |
| WO | 9812979 | 4/1998 |
| WO | 9911325 | 3/1999 |
| WO | 9933515 | 7/1999 |
| WO | 9942163 | 8/1999 |
| WO | WO 02/089899 A1 | 11/2002 |
| WO | WO2004/049918 | 6/2004 |
| WO | WO 2004/049918 A2 | 6/2004 |

OTHER PUBLICATIONS

Chun, M. et al. "Interstitial Iridium-192 Implantation for Malignant Brain Tumours. Part II: Clinical Experience," *The British Journal of Radiology*, vol. 62, 158-62 (1989).

Garfield, J. et al., "Postoperative Intracavitary Chemotherapy of Malignant Gliomas," *J. Neurosurg.*, vol. 39 315-22 (Sep. 1973).

Gutin, P. et al., "Brachytherapy of Recurrent Malignant Brain Tumors With Removable High-Activity Iodine-125 Sources," *J. Neurosurg.*, vol. 60, 61-8 (1984).

Johannesen, T.B. et al., "Intracavity Fractionated Balloon Brachytherapy in Glioblastoma," *Acta Neurochir (Wien)* vol. 141, 127-33 (1999).

Leibel, S. et al., "The Integration of Interstitial Implantation Into the Preliminary Management of Patients With Malignant Gliomas: Results of a Phase II Northern California Oncology Group Trial," *Am. J. Clin. Oncol. (CCT)*, vol. 10, No. 2, p. 106 (1987).

Roberts, D. et al., "Interstitial Hyperthermia and Iridium Brachytherapy in Treatment of Malignant Glioma," *J. Neurosurg.*, vol. 64, 581-7 (1986).

Wu, A. et al., "Interstitial Iridium-192 Implantation for Malignant Brain Tumours. Part 1: Techniques of Dosimetry Planning," *The British Journal of Radiology*, vol. 62, 154-7 (1989).

* cited by examiner

DRUG ELUTING BRACHYTHERAPY METHODS AND APPARATUS

BACKGROUND OF THE INVENTION

This invention relates generally to methods and apparatus for use in treating proliferative tissue disorders, and more particularly to the treatment of such disorders with a drug eluting brachytherapy device.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary brachytherapy. The term "brachytherapy," as used herein, refers to radiation therapy delivered by a source of therapeutic rays inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

Williams U.S. Pat. No. 5,429,582, entitled "Tumor Treatment," describes a method and apparatus for treating tissue surrounding a surgically excised tumor with radioactive emissions to kill cancer cells that may be present in the tissue surrounding the excised tumor. In addition to the radioactive emissions, Williams discloses external transmitters that can deliver heat to the surrounding tissue, and a permeable balloon through which chemotherapy drugs can seep. Although this device may be effective, permeable materials present some challenges. The permeable materials must be manufactured to precise standards to achieve consistent permeability, and in use, controlling the delivery rate of the chemotherapy drugs can be complicated. Since the delivery rate is dependent on the pressure provided on the chemotherapy drugs, administering the drugs requires extra equipment and attention. In addition, the drugs are delivered uniformly in all directions and cannot be focused on desired regions.

SUMMARY OF THE INVENTION

The present invention generally provides a drug eluting brachytherapy device including an insertion member having a proximal portion, a distal portion, and at least one lumen extending therethrough. An expandable surface member is mated to the distal portion of the insertion member and defines a spatial volume therein. The device further includes a treatment agent releasably mated with the expandable surface member. When the device is positioned within a tissue cavity at least a portion of the treatment agent is delivered to adjacent tissue.

The treatment agent positioned on the expandable surface member allows a user to directly deliver drugs to adjacent tissue. In one aspect of the invention, the treatment agent is positioned in a layer on the surface of the expandable surface member and is delivered to tissue surrounding a resected tissue cavity by expansion of the expandable surface member within the tissue cavity. In addition to a treatment agent, the brachytherapy device includes a radiation source for delivering radiation to the target tissue surrounding the tissue cavity. The radiation source is preferably disposed within the expandable surface member.

Another embodiment of the present invention includes a drug eluting tissue positioning device for positioning target tissue surrounding a resected tissue cavity and delivering radiation from an external radiation source. The device includes a catheter body member having proximal and distal portions, an expandable surface member with a treatment agent releasably mated to the outer surface, and an external radiation source. Expansion of the expandable surface element within a resected tissue cavity delivers the treatment agent and positions the surrounding tissue for receiving a radiation beam from the external radiation source.

In another embodiment of the present invention, a method for delivering a treatment material is provided. The method includes providing a drug eluting brachytherapy device having an insertion member with a proximal portion and a distal portion. An expandable surface member defining a spatial volume is disposed on the insertion member and a treatment agent is releasably mated with the expandable surface member. The method further includes positioning the brachytherapy device within a tissue cavity and delivering the treatment agent to tissue surrounding the tissue cavity.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides methods and apparatus for treating proliferative tissue disorders, such as malignant tumors of the breast, with an interstitial, drug eluting brachytherapy device. The brachytherapy device includes an insertion member having a proximal portion, a distal portion and at least one lumen extending therethrough. An expandable surface member, having a treatment agent releasably mated therewith, is mated to the distal portion of the insertion member and defines a spatial volume therein. When the brachytherapy device is positioned in a resected tumor cavity for radiation therapy, at least a portion of the treatment agent is delivered to adjacent tissue.

Many brachytherapy procedures typically involve first removing at least part of the proliferative tissue, e.g. cancerous tumor, and then placing a device into the resected tissue cavity for delivering radiation to the adjacent tissue. The present invention provides an improved brachytherapy device for delivering treatment agents, such as chemotherapy drugs, to the adjacent tissue directly from the surface of the device. Surface delivery provides the user with more control over delivery because the treatment agent can be placed in direct physical contact with target tissue. This provides an advantage because the effectiveness of some treatment agents depends on direct delivery to the target tissue area. In addition, by delivering a treatment agent in close proximity to the target areas, dilution is minimized. Many treatment agents are toxic to the human body, especially when delivered systemically, and thus delivery from the surface of the brachytherapy device also minimizes exposure to healthy areas. A drug eluting surface is also an improvement over other more complicated delivery methods, such as delivery through a permeable membrane that requires precise fabrication of the membrane and careful pressure control of the delivered substance. The present invention therefore provides a number of advantages over prior art devices.

Figure 1:
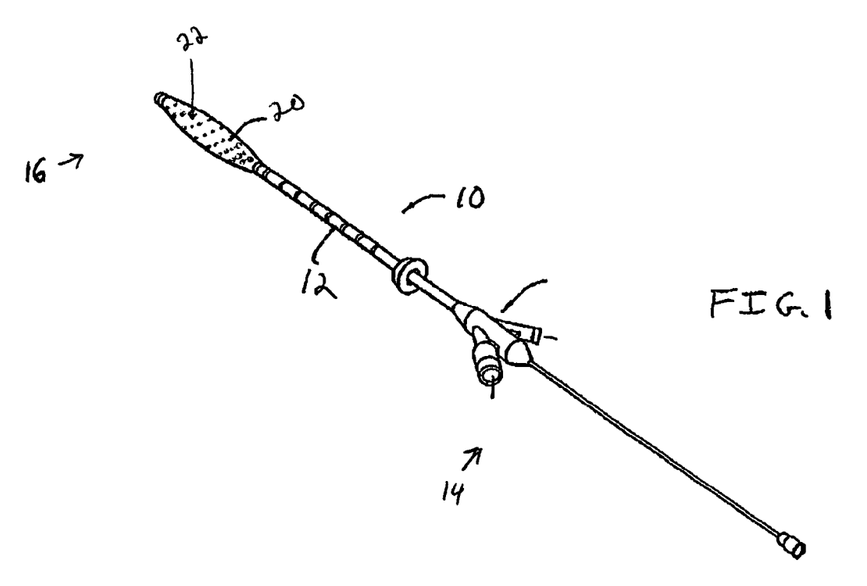
FIG. 1 illustrates a perspective view of the brachytherapy device of the present invention.

FIG. 1 illustrates one embodiment of the present invention including a drug eluting brachytherapy device 10 having an insertion member 12 with a proximal portion 14, a distal portion 16, and at least one lumen 18 (not shown) extending therethrough. An expandable surface member 20 is mated to the distal portion of insertion member 12. The expandable surface member defines a spatial volume 24 therein and includes a treatment agent 22 releasably mated therewith. When device 10 is inserted into a resected tissue cavity at least a portion of treatment agent 22 is delivered to adjacent tissue.

As shown in FIG. 1, the treatment agent is preferably mated with expandable surface member 20 because the expandable surface member contacts the walls of the resected tissue cavity after insertion of device 10 and expansion of expandable surface member 20. The treatment agent preferably is layered on the surface of expandable surface member 20 such that when the expandable surface member is expanded to contact tissue, at least part of the treatment agent is released. In an alternative embodiment, the treatment agent can be at least partly embedded in the sidewall of expandable surface member 20 such that as the expandable surface member expands the treatment agent is released and/or diffuses out. Regardless, at least some of treatment agent 22 moves from the expandable surface member to tissue, without passing through the expandable surface member.

In one embodiment, multiple layers are applied to the surface of expandable surface member 20. Each layer may have the same treatment agent such that the layers effectively represent one thick layer. Alternatively, different concentrations of the treatment agent or different treatment agents may be found in different layers. By positioning different treatment agents in different layers, the device can deliver different treatment agents as needed during the treatment procedure. For example, the first outer layer or layers could have a chemotherapy drug that is delivered to the adjacent tissue after insertion of device 10. Subsequently, an antibiotic drug could be administered from an inner layer so that it is received by the surrounding tissue shortly before withdrawal of device 10. Having the first layer as an inert/inactive substance with its release prior to exposure of the active substance represents a method of delayed or timed release of the therapeutic substance.

Figure 2:
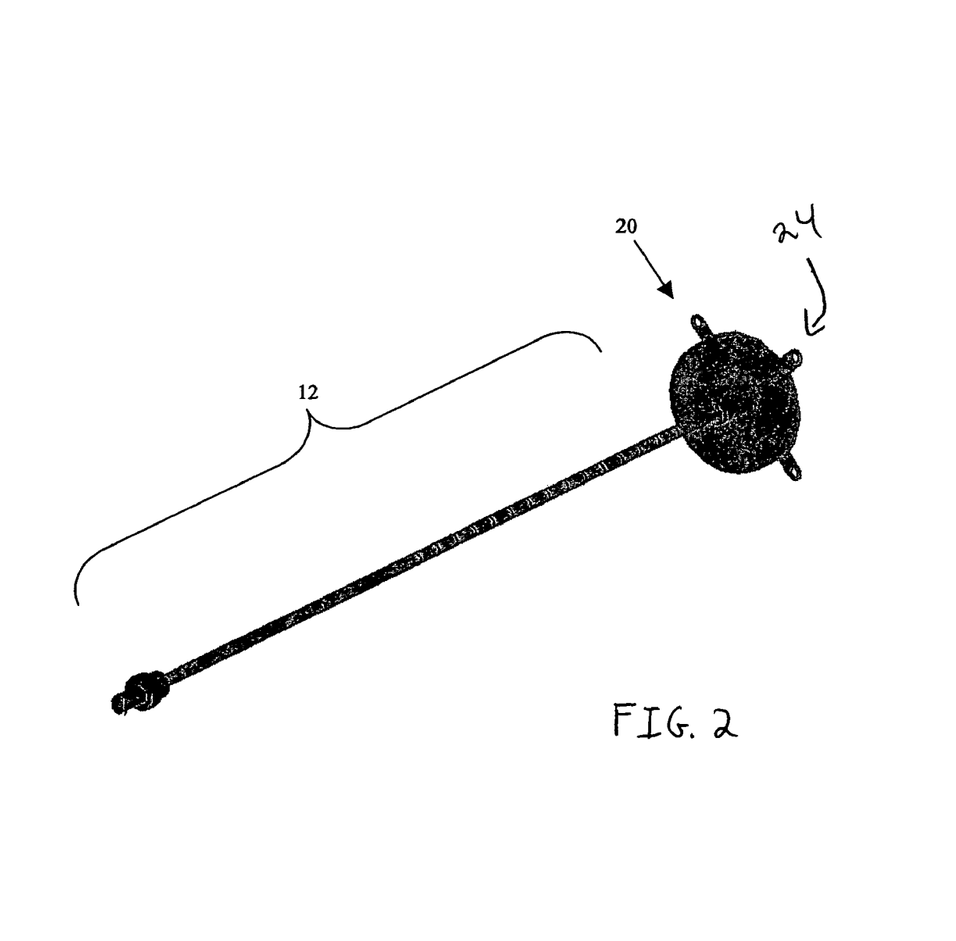
FIG. 2 illustrates another embodiment of the brachytherapy device of the present invention shown in perspective.

The treatment agent can also be mated with only a portion of the expandable surface member to limit the treatment delivered to certain areas of the surrounding tissue. For example, partial coverage of expandable surface member 20 is beneficial when some of the tissue surrounding device 10 is sensitive to the treatment agent. Device 10 can be positioned within the tissue cavity such that the area covered with a treatment agent is not in contact with the sensitive tissue and the treatment agent is not delivered to the sensitive tissue. Partial coverage is also preferable for brachytherapy devices that focus their treatment on a tissue surface. FIG. 2 illustrates a brachytherapy device 10 having treatment surface 26 (not shown) which is shaped to conform to a predetermined surface area of a tissue to be treated. The device includes insertion member 12 and expandable surface 20 with treatment agent 22 releasably positioned on treatment surface 26. In use, the treatment surface is positioned against target tissue and the treatment agent is delivered. Preferably, treatment agent 22 is not mated with other portions of the expandable surface member because those other portions do not contact target tissue.

Figure 3:
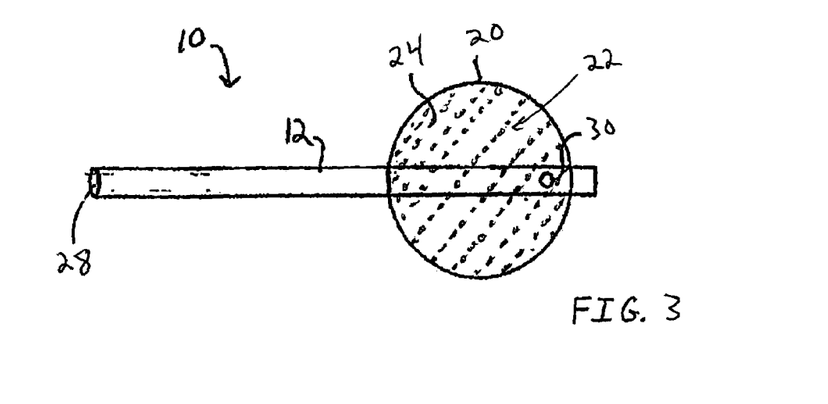
FIG. 3 illustrates another embodiment of the brachytherapy device of the present invention shown in a full view.

FIGS. 3 through 8 illustrate other exemplary brachytherapy devices 10 that can include a treatment agent releasably mated thereon. FIG. 3 shows a basic design of a tissue positioning device 10, including insertion member 12 having an inner lumen 18 extending from proximal port 28 to inflation port 30. Inflation port 30 is formed through the sidewall of insertion member 12 and intersects with inner lumen 18. Affixed to insertion member 12, proximate to a distal end thereof, is a spatial volume 24 that is defined by an expandable surface member 20. The interior of expandable surface member 20 is in fluid communication with proximal port 28. Treatment agent 22 is releasably mated with the expandable surface member.

Expandable surface member 20 of device 10 can be defined by an inflatable balloon. It will be understood that the term "balloon" is intended to include distensible devices which can be, but need not be, constructed of an elastic material. The balloon of the present invention may include the variety of balloons or other distensible devices designed for use with surgical catheters. The balloon can be expanded by injecting an inflation material through insertion member 12 and into the balloon. The inflation material can include a radioactive treatment material where the balloon will be used to provide interstitial brachytherapy treatment as is provided in U.S. Pat. Nos. 5,611,923 and 5,931,774 to Williams et al, both of which are incorporated by reference herein.

In one embodiment, the balloon is constructed of a solid material that is substantially impermeable to active components of a treatment fluid with which it can be filled, and is also impermeable to body fluids, e.g., blood, cerebrospinal fluid, and the like. An impermeable balloon is useful in conjunction with a radioactive treatment fluid, to prevent the radioactive material from escaping the treatment device and contaminating the surgical field or tissues of the patient.

In another embodiment, the balloon is permeable to a treatment fluid, and permits a treatment fluid to pass out of device 10 and into a body lumen or cavity. A permeable balloon is useful for delivering a fluid treatment agent through the balloon wall. U.S. Pat. Nos. 6,200,257 and 6,537,194 to Winkler disclose exemplary permeable balloons and treatment substances. Where treatment agent 22 is positioned over the permeable balloon wall it will preferably block the passage of treatment fluid until after treatment agent 22 has released from the expandable surface member. Alternatively, part of the permeable balloon wall may be free of treatment material.

Figure 4A:
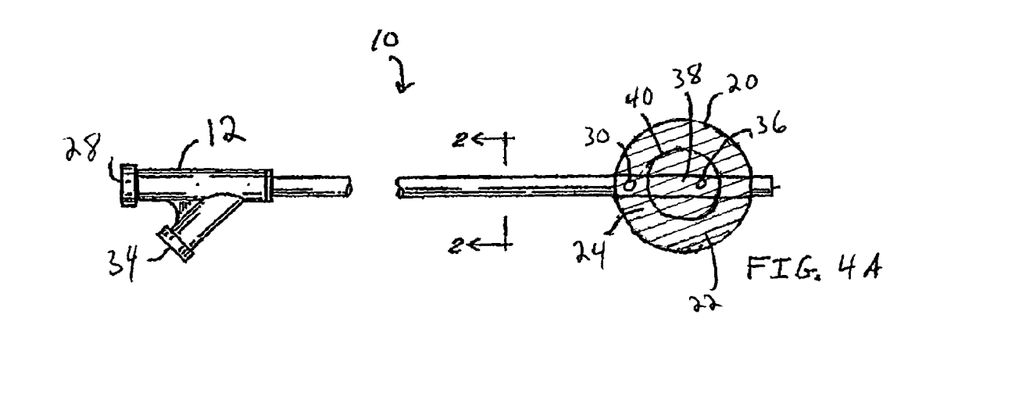
FIG. 4A illustrates another embodiment of the brachytherapy device of the present invention shown in a full view.
Figure 4B:
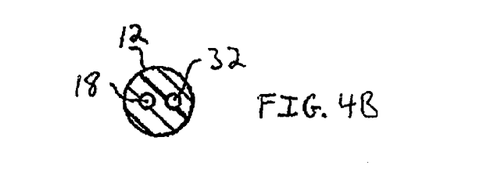
FIG. 4B illustrates a cross sectional view of the device pictured in FIG. 4A.
Figure 5:
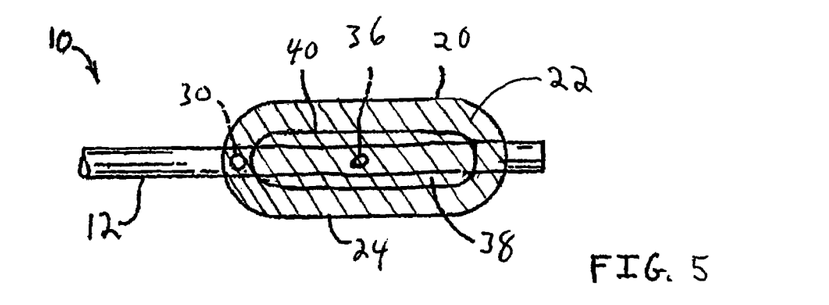
FIG. 5 illustrates another embodiment of the brachytherapy device of the present invention shown in a full view.

The invention also contemplates the use of multiple balloons, e.g., a double-walled structure as shown in FIGS. 4A and 5. FIGS. 4A and 5 illustrate a double-walled balloon brachytherapy device 10 for treatment to proliferative tissue. Device 10 includes a insertion member 12 having first and second lumens 18 and 32 (FIG. 4B) extending from proximal ports 28 and 34 to inflation ports 30 and 36 formed through the side wall of the insertion member 12 and intersecting with the lumens 18 and 32, respectively.

Affixed to insertion member 12 proximate to the distal end thereof is an inner spatial volume 38 which may be defined by a generally spherical inner wall 40 of an outer spatial volume 24. The interior of the inner volume 38 is in fluid communication with inflation port 36. Surrounding inner spatial volume 38 is an outer spatial volume 24 defined by a spherical expandable outer wall 20 that is appropriately spaced from the inner wall 40 of the inner spatial volume 38 when the two volumes are inflated or otherwise supported. Outer volume 24 encompasses inflation port 30. The embodiments of FIGS. 4A and 5 include inner and outer spatial volumes 38 and 24 respectively, one inside the other. The outer spatial volume 24, being the volume defined by the space between the inner spherical wall 40 and the outer spherical expandable wall 20 may be filled with air, or a radiation absorbing fluid, such as a contrast media. The inner spatial volume 38 may be filled with a treatment fluid for delivering radiation from inner spatial volume 38 to tissue surrounding the outer wall 20 or it may contain other radiation sources. U.S. Pat. No. 6,413,204 to Winkler et al. describes multi-walled balloons used in brachytherapy devices for treating proliferative tissue disorders and is hereby incorporated by reference in its entirety.

As shown in FIGS. 4A and 5, a treatment agent 22 is releasably mated with the surface of the outer balloon. As the device is inflated within a tissue cavity, the treatment agent on the wall of the outer balloon will contact the surrounding tissue and the treatment agent will be delivered to the target tissue. Preferably, the treatment agent completely covers the outer balloon wall such that the tissue cavity receives a uniform dose of the treatment agent.

Insertion member 12 of device 10 provides a means for positioning expandable surface member 20 within the resected tissue cavity and provides a path for delivering inflation material (if used). Although the exemplary insertion member illustrated in the FIGS. has a tubular construction, one of skill in the art will appreciate that insertion member 12 can have a variety of shapes and sizes. Insertion members suitable for use in the invention can include catheters which are known in the art. Although insertion member 12 can be constructed of a variety of materials, in one embodiment the insertion member material is silicone, preferably a silicone that is at least partially radio-opaque, thus facilitating x-ray location of insertion member 12 after insertion of device 10. Insertion member 12 can also include conventional adapters for attachment to a treatment fluid receptacle and the balloon, as well as devices, e.g., right-angle devices, for conforming insertion member 12 to contours of the patient's body.

Although the balloon and body member 12 can mate in a variety of ways, in some embodiments, the balloon is mated to body member 12 at substantially a single point on, or a single side of, the balloon body. Such attachment permits the balloon (e.g., a spherical balloon) to maintain a substantially constant (e.g., spherical) shape over a range of inflation volumes. That is, the balloon is not constrained in shape by multiple attachment points to the body member, as is commonly the case with, e.g., balloons for Foley catheters.

Figure 6A:
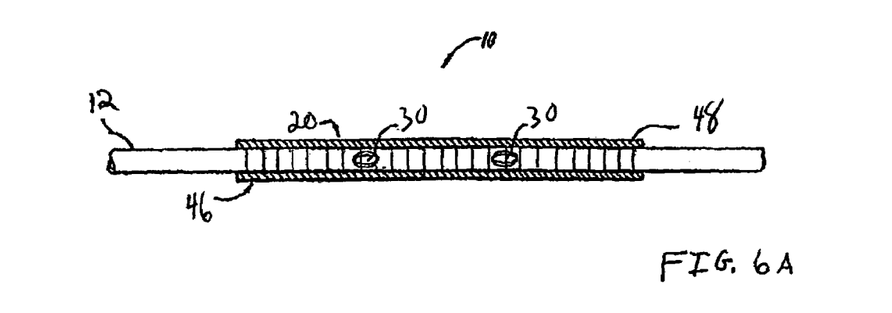
FIG. 6A illustrates another embodiment of the brachytherapy device of the present invention shown in a full view.
Figure 6B:
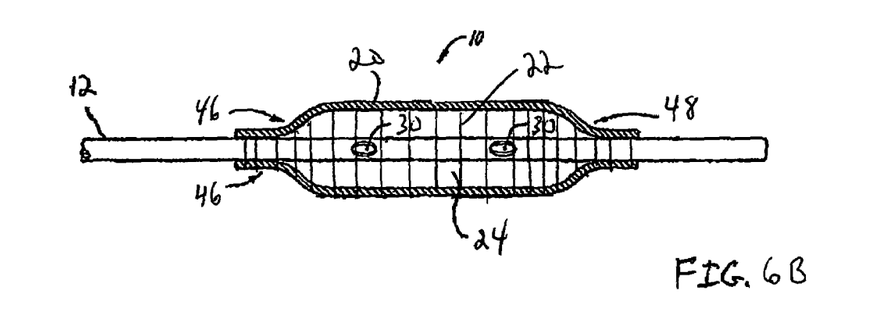
FIG. 6B illustrates the device of FIG. 6A in an expanded position.

In another embodiment, the expandable surface member is fixed to insertion member 12 at both ends of expandable surface member 20 as shown in FIGS. 6A and 6B. The illustrated embodiment includes an elongated insertion member 12 having at least one inner lumen 18 extending the length thereof from a proximal end to a distal end. Openings in the sidewall of insertion member 12 define one or more inflation ports 30 that provide fluid communication between inner lumen 18 and a spatial volume 24. Expandable surface 20 can be attached to the tubular insertion member 12 by bonding the proximal and distal ends 44, 46 of the expandable surface member 20 to the insertion member 12. As shown in FIG. 6B, injecting an inflation material into the proximal end of insertion member 12 forces the inflation material to flow through inner lumen 18, out the inflation ports 30, and to fill spatial volume 24 within expandable surface 20, thereby inflating expandable surface 20. The treatment agent 22 disposed on expandable surface member 20 is then in position to contact tissue and be released to the target tissue area.

Figure 7A:
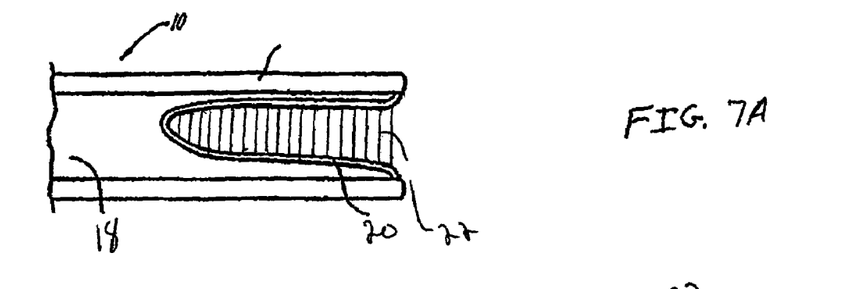
FIG. 7A illustrates another embodiment of the brachytherapy device of the present invention shown in a full view.
Figure 7B:
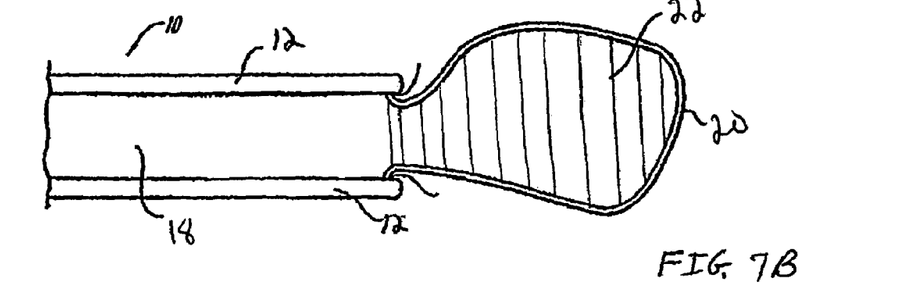
FIG. 7B illustrates the device of FIG. 7A in an expanded position.

In FIG. 7A, yet a further embodiment of device 10 is depicted having an expandable surface 20 which resides within inner lumen 18 of tubular body 12. In this embodiment, treatment agent 22 releasably positioned on expandable surface member 20 is at least partly protected from tissue contact prior to inflation of the expandable surface member because the expandable surface member is disposed within insertion member 12. As shown, inner lumen 18 extends the length of body 12 and expandable surface 20 is fixedly attached at distal end of insertion member 12. As an inflation material is injected through inner lumen 18, expandable surface 20 expands outwardly from tubular body 12 as shown in FIG. 7B. With the expandable surface expanded, the treatment material disposed on the expandable surface member is in position to contact tissue and release the treatment material. This device may be particularly advantageous wherein there is a concern about the treatment material being accidentally delivered to healthy tissue during insertion of device 10.

Figure 8:
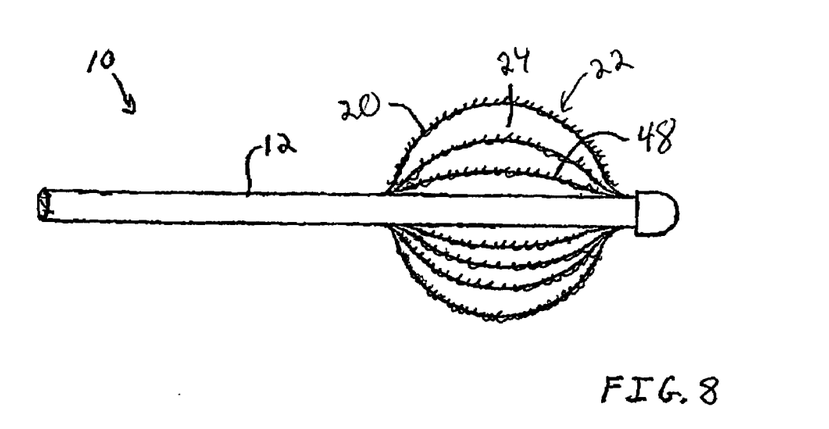
FIG. 8 illustrates another embodiment of the brachytherapy device of the present invention shown in a full view.

Expandable surface member 20 can be defined by a variety of structures, including a cage 48 as illustrated in FIG. 8. The pictured device 10 includes a body member 12 and an expandable surface 20, with the expandable surface being defined by cage 48, positioned proximal to the distal end of body member 12. Preferably, cage 48 is formed from a shape memory metal, such a nitinol, or a suitable plastic, such as an expandable polyethylene cage. In use the cage can be formed in the desired shape to conform to a particular resected cavity, contracted for delivery to the target site in vivo, and then expanded to cause the tissue surrounding the surgically resected region to take the appropriate shape. In this case, treatment agent 22 is releasably mated with the cage and will be at least partly released when the cage contacts tissue.

Treatment agent 22 of the present invention can include any of the materials used for the treatment of proliferative tissue disorders. In addition, the treatment agent can represent any of the substances used to treat tissue during surgical procedures, such as agents which speed healing and/or help to prevent infection. In one embodiment, the treatment agent includes a material selected from the group consisting of, a chemotherapy drug, an anti-neoplastic agent, an anti-angiogenesis agent, an immunomodulator, a hormonal agent, an immunotherapeutic agent, an antibiotic, a pain-reliever, and combinations thereof.

The treatment agent can be mated with expandable surface member 20 in a variety of ways as long as the treatment agent is at least partly released when contacted by tissue within a resected tissue cavity. For example treatment agent 22 can be mated by heat bonding, solvent bonding, with an adhesive, adsorbed layers of active and inactive material providing for timed release of the active ingredient, chemical bonding, bonding that can be released by mechanical means (e.g., stretching of the applicator surface, changes in treating surface temperature or electrical charge). In addition, the treatment agent may be mixed with a binding agent to help affix the treatment agent to the expandable surface member. The binding agent preferably includes biocompatible polymers, and even more preferably bioresorbable polymers, such as for example poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. A person of skill in the art will appreciate that the treatment agent can be bound to the expandable surface member in a variety of ways as long as the binding method allow at least partial release of the binding agent into the tissue surrounding a resected tissue cavity.

The rate of delivery for the treatment agent will depend on a number of factors including the other material mixed with the treatment agent, the concentration of the treatment agent, the characteristics of the treatment agent and the type of expandable surface member used with the treatment material. A person of skill in the art will appreciate that the time of delivery and the rate of delivery can be adjusted based on these and other factors.

In addition to the treatment agent, other materials may be disposed on the expandable surface member to assist with binding or delivering treatment agent 22. For example, a coating layer can cover a treatment agent containing layer to reduce the chance of losing treatment agent during the insertion process. The coating layer can be produced from the bioresorbable materials listed above so that after insertion of device 10, the coating layer will resorb and expose a layer containing the treatment agent.

A method of the present invention can be used to treat a variety of proliferative tissue disorders including primary malignancies, mestastic lesions, malignant breast and brain tumors. Many breast cancer patients are candidates for breast conservation surgery, also known as lumpectomy, a procedure that is generally performed on early stage, smaller tumors. Breast conservation surgery may be followed by radiation therapy to reduce the chance of recurrences near the original tumor site. Providing a strong direct dose to the effected area can destroy remaining cancer cells and help prevent such recurrences.

Surgery and radiation therapy are also the standard treatments for malignancies which develop in other areas of the body such as brain tumors. The goal of surgery is to remove as much of the tumor as possible without damaging vital brain tissue. The ability to remove the entire malignant tumor is limited by its tendency to infiltrate adjacent normal tissue. Partial removal reduces the amount of tumor to be treated by radiation therapy and, under some circumstances, helps to relieve symptoms by reducing pressure on the brain.

A method according to the invention for treating these and other malignancies begins by surgical resection of a tumor site to remove at least a portion of the cancerous tumor and create a resection cavity. Following tumor resection, device 10 is placed into the tumor resection cavity. This can occur prior to closing the surgical site such that the surgeon intraoperatively places the device, or alternatively device 10 can be inserted once the patient has sufficiently recovered from the surgery. In the later case, a new incision for introduction of device 10 can be created. In either case, expandable surface 20 is then expanded within the resected tissue cavity.

Treatment agent 22 disposed on the expandable surface member is delivered to the tissue surrounding the tissue cavity as the expandable surface member expands. In one embodiment, the treatment agent is a chemotherapy drug which is delivered to the surrounding tissue to treat any remaining proliferative tissue. In some embodiments, multiple treatment agents are delivered to the surrounding tissue to treat the target tissue and to help the healthy tissue recover from surgery.

Radiation is also preferably delivered to the target tissue surrounding device 10. The radiation source of the present invention preferably includes any radiation source which can deliver radiation to treat proliferative tissue disorders. Exemplary radiation sources include high dose brachytherapy radiation, medium dose brachytherapy radiation, low dose brachytherapy radiation, pulsed dose rate brachytherapy radiation, external beam radiation, and combinations thereof.

Radiation can be delivered from inside expandable surface member 20, as discussed above, as well as from an external radiation source. Internal radiation embodiments include delivering a symmetric isodose curve as disclosed in U.S. Pat. No. 6,413,204 to Winkler et al., hereby incorporated by reference in its entirety. Additional internal radiation treatments can include an asymmetric radiation profile as disclosed in U.S. Pat. No. 6,482,142 to Winkler et al, hereby incorporated by reference in its entirety.

Alternatively, an external radiation source can be used. In one embodiment, the device of the present invention is a drug eluting tissue positioning device for treating a proliferative tissue disease with external radiation. The device includes a catheter body member having proximal and distal portion, and an expandable surface member defining a spatial volume, and an external radiation source. A treatment agent is releasable mated with the expandable surface member for delivery to tissue surrounding a resected tissue cavity. When the expandable surface member is positioned in the resected tissue cavity and expanded, it not only delivers the treatment agent, but also positions the surrounding tissue for receiving a therapeutic ray from the external radiation source. U.S. Pat. Application entitled TISSUE POSITIONING SYSTEMS AND METHODS FOR USE WITH RADIATION THERAPY, Ser. No. 10/704,161 discloses exemplary external radiation treatment methods and devices and is hereby incorporated by reference in its entirety.

A person of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

The invention claimed is:

1. A drug eluting brachytherapy device, comprising:
   (a) an insertion member having a proximal portion, a distal portion, and at least one lumen extending therethrough:
   (b) an expandable surface member mated to the distal portion of the insertion member and defining a spatial volume therein, wherein said spatial volume is configured to receive a radiation source therein to enable a three-dimensional isodose profile that is substantially similar in shape to said expandable surface member; and
   (c) a plurality of treatment releasably mated with an outer surface of the expandable surface member; wherein at least a portion of each of the treatment agents is delivered to adjacent tissue when the brachytherapy device is positioned within a tissue cavity, and wherein a first treatment agent begins delivery before a second treatment agent.

2. The device of claim 1, wherein the expandable surface member is a fluid retaining expandable surface member.

3. The device of claim 1, wherein at least one treatment agent is nonradioactive.

4. The device of claim 1, wherein the treatment agents are coated on the outer surface of the expandable surface member.

5. The device of claim 4, wherein different treatment agents are disposed in different layers.

6. The device of claim 1, wherein at least one treatment agent is dispersed within a sidewall of the expandable surface member.

7. The device of claim 1, wherein at least one treatment agent is disposed on only a portion of the surface of the expandable surface member.

8. The device of claim 7, wherein the at least one treatment agent is disposed on less then about half the surface of the expandable surface member.

9. The device of claim 1, wherein the expandable surface member includes a first surface adapted for positioning against a tissue surface.

10. The device of claim 9, wherein at least one treatment agent is disposed only on the first surface.

11. The device of claim 1, wherein each treatment agent is selected from the group consisting of, a chemotherapy drug, an anti-neoplastic agent, an anti-angiogenesis agent, an immunomodulator, a hormonal agent, an immunotherapeutic agent, a pain reliever, an antibiotic or combinations thereof.

12. The device of claim 1, wherein at least one of the treatment agents is mixed with a binding agent.

13. The device of claim 12, wherein the binding agent is a bioresorbable polymeric binding agent.

14. A drug eluting tissue positioning device for positioning target tissue surrounding a resected tissue cavity so that the target tissue can receive a measured radiation dose, comprising:
   a catheter body member having a proximal portion and a distal portion;
   an expandable surface member, the expandable surface member defining a spatial volume therein, wherein said spatial volume is configured to receive a radiation source therein; and
   a plurality of treatment releasably mated with an outer surface of the expandable surface member; wherein at least a portion of each treatment agent is delivered to tissue surrounding the resected tissue cavity when the device is positioned within the resected tissue cavity, and wherein a first treatment agent begins deliver to the tissue before a second treatment agent begins delivery.

15. The device of claim 14, wherein the expandable surface member is constructed of a material permeable to a treatment agent.

16. The device of claim 15, wherein a third treatment agent capable of permeating through the walls of the expandable surface member is disposed within the expandable surface member.

17. The device of claim 16, wherein a fluid delivery path for the delivery of the third treatment agent extends through the catheter body member into the spatial volume within the expandable surface member, and out through the permeable expandable surface member.

18. The device of claim 14, wherein the expandable surface member includes permeable and nonpermeable portions, and the treatment agents are mated with only the nonpermeable portions.

19. The device of claim 14, wherein each treatment agent is selected from the group consisting of, a chemotherapy drug, an anti-neoplastic agent, an anti-angiogenesis agent, an immunomodulator, a hormonal agent, an immunotherapeutic agent, an antibiotic or combinations thereof.

20. The device of claim 14, wherein a radiation source is disposed within the expandable surface member.

21. The device of claim 14, wherein an external radiation source is disposed outside of the expandable surface member.

22. A method of delivering a treatment material, comprising:
   providing a drug eluting brachytherapy device having a catheter body member with a proximal portion and a distal portion, an expandable surface member defining a spatial volume, and a plurality treatment agents releasably mated with an outer surface of the expandable surface member;
   positioning the brachytherapy device within a tissue cavity; and
   delivering the treatment agents to tissue surrounding the tissue cavity, wherein a first treatment agent begins releasing before a second treatment agent begins releasing.

23. The method of claim 22, wherein the tissue cavity is a resected tissue cavity created during a lumpectomy procedure.

24. The method of claim 22, wherein at least one treatment agent is a chemotherapy drug.

25. The method of claim 22, wherein the plurality of treatment agents are layered on the outer surface of the expandable surface member and the first treatment agent is disposed in an outer layer and the second treatment agent is disposed in an inner layer.

26. The method of claim 22, wherein the tissue cavity is a naturally occurring cavity.

27. The method of claim 26, wherein the cavity is selected from the group consisting of the bladder, the esophagus, the gut, the urethra, and the ureters.

28. The method of claim 22, wherein the tissue cavity is mechanically formed.

* * * * *